(12) United States Patent
Matsuzaki et al.

(10) Patent No.: US 7,238,209 B2
(45) Date of Patent: Jul. 3, 2007

(54) BONE REPLACEMENT MATERIAL

(75) Inventors: Hiromi Matsuzaki, 33-6, Kamitakada 4-chome, Nakano-ku, Tokyo (JP); Yoshie Tominaga, Saitama (JP)

(73) Assignees: PENTAX Corporation, Tokyo (JP); Hiromi Matsuzaki, Tokyo (JP)

( * ) Notice: Subject to any disclaimer, the term of this patent is extended or adjusted under 35 U.S.C. 154(b) by 0 days.

(21) Appl. No.: 10/457,484

(22) Filed: Jun. 10, 2003

(65) Prior Publication Data

US 2004/0010314 A1    Jan. 15, 2004

(30) Foreign Application Priority Data

Jun. 12, 2002    (JP)    .............. 2002-171814

(51) Int. Cl.
*A61F 2/28* (2006.01)
(52) U.S. Cl. ............... 623/23.61; 623/17.11; 623/23.73; 606/92
(58) Field of Classification Search ............ 623/23.61, 623/23.56, 16.11, 23.74, 23.62, 23.51, 17.11, 623/23.73; 606/92, 93, 94
See application file for complete search history.

(56) References Cited

U.S. PATENT DOCUMENTS

| | | | |
|---|---|---|---|
| 4,889,833 A | | 12/1989 | Nakamura et al. |
| 6,187,046 B1 | | 2/2001 | Yamamoto et al. |
| 6,203,574 B1 | | 3/2001 | Kawamura |
| 6,387,130 B1 | * | 5/2002 | Stone et al. ............. 623/17.16 |
| 6,440,444 B2 | * | 8/2002 | Boyce et al. ............. 424/422 |
| 6,725,083 B1 | * | 4/2004 | Burbank et al. ............. 600/431 |
| 2002/0026242 A1 | * | 2/2002 | Boyle et al. ............. 623/17.11 |
| 2003/0060892 A1 | | 3/2003 | Richter et al. |

FOREIGN PATENT DOCUMENTS

| | | |
|---|---|---|
| DE | 3937361 | 5/1991 |
| EP | 0263489 | 4/1988 |
| GB | 2237564 | 5/1991 |
| JP | 61127658 | 6/1986 |
| JP | 2958037 | 10/1999 |
| JP | 2000084062 | 3/2000 |

(Continued)

OTHER PUBLICATIONS

Mathworld, Parallelepiped, http://mathworld.wolfram.com, 1999 CRC Press LLC.*

(Continued)

Primary Examiner—Bruce Snow
(74) Attorney, Agent, or Firm—Greenblum & Bernstein, P.L.C.

(57) ABSTRACT

A bone replacement material for use in a treatment for repairing a vertebral body compression fracture is formed into a pellet having a roughly polyhedral shape. Each pellet having the roughly polyhedral shape has a pair of opposite surfaces, in which one of the opposite surfaces is inclined with respect to the other surface for a predetermined angle. The angle is preferably in the range of 10 to 60°. Further, the volume of each pellet of the bone replacement material 1 is in the range of 13 to 239 mm3. Furthermore, the bone replacement material is formed of calcium phosphate based compound having the Ca/P ratio of 1.0 to 2.0. By using such a bone replacement material, it is possible to carry out packing operation of the bone replacement material into a collapsed vertebral body smoothly, reliably and safely.

15 Claims, 14 Drawing Sheets

FOREIGN PATENT DOCUMENTS

JP      2000107585      4/2000
WO      02/060504       8/2002

OTHER PUBLICATIONS

Volumne of a 3D Parallelepiped, http://www.plmsc.psu.edu, EDT 1996.*
English Language Abstract of JP2000-084062.
English Language Abstract of DE3937361.
English Language Abstract of JP2000-107585.
English Language Translation of JP Appln. No. 2958037.
English Language Abstract of 61-127658.
Database WPI Derwent Publication Ltd., London XP002347348.
Database WPI Derwent Publication Ltd., London XP002347349.

* cited by examiner (A)

(B)

(A)

(B)

(A)

(B)

(A)

(B)

BONE REPLACEMENT MATERIAL

BACKGROUND OF THE INVENTION

1. Field of the Invention

This invention relates to a bone replacement material.

2. Description of the Prior Art

Collapse of a vertebral body as a result of trauma or osteoporosis is referred to as a vertebral body compression fracture. In the method that is known for the treatment of this kind of fracture, the collapsed vertebral body is repaired by filling the inside thereof with a filler (such as a bone replacement material) through a vertebral arch using a transpedicular technique.

In this treatment method, a collapsed vertebral body is first returned to a substantially original shape, that is, a collapsed vertebral body is reduced, whereby a cavity is created therein. A filler such as a bone replacement material is then inserted into the cavity to repair the vertebral body.

Conventionally, in such a treatment method, the inside of the collapsed vertebral body is filled with a granular bone replacement material using a cylindrical member having a hollow passage extending from the proximal end to the distal end thereof.

However, when such a conventional bone replacement material is used, the hollow passage of the cylindrical member is likely to be clogged with the bone replacement material, so that there is a case that it is difficult to smoothly perform such a filling operation. Such clogging occurs due to the following reasons. Namely, since such a granular bone replacement material is formed by grinding blocks of the bone replacement material, shapes of the particles are not uniform, so that such a granular bone replacement material has poor fluidity. Further, the particles of the granular bone replacement material include relatively small particles of which diameter is less than 1 mm. Such small particles are likely to enter the space between the inner surface of the hollow passage and the outer surface of an ejector bar which is inserted into the hollow passage. Such small particles entering into the space is liable to give an adverse effect to the slidability of the ejector bar with respect to the hollow passage. For these reasons, when such a conventional bone replacement material is used, the hollow passage of the cylindrical member is likely to be clogged with the bone replacement material.

Further, when the conventional bone replacement material is used, the bone replacement material introduced into the cavity of the vertebral body is likely to remain near an opening of the distal end of the cylindrical member, thus it is difficult to pack a sufficient amount of the bone replacement material into the cavity. Furthermore, even when the cavity is filled with a large amount of the bone replacement material, it is difficult to increase the filling factor sufficiently due to the presence of many gaps among the granules. Moreover, the granular bone replacement material is not always to have a spherical shape, namely, some of the granules are formed with protrusions on their surfaces. Such granules are likely to be broken when a load is applied thereto, so that the volume of the vertebral body is diminished. As a result, it is difficult to keep the result of the operation over a long period of time.

Further, in addition to the above method, there is another method which uses a bone replacement material (bone cement) that has fluidity when it is introduced into a vertebral body but will be hardened in the vertebral body. However, when such a material is used, there is a risk that the material will flow out from the vertebral body to damage adjacent nerves, thus problems still remain in its safeness.

SUMMARY OF THE INVENTION

It is an object of the present invention to provide a bone replacement material by which a packing or filling operation to a collapsed vertebral body can be carried out smoothly, reliably and safely.

In order to achieve the above object, the present invention is directed to a bone replacement material for use in a treatment for repairing a vertebral body compression fracture, wherein the bone replacement material is formed into a pellet (or a small block) having a roughly polyhedral shape.

Use of such a bone replacement material makes it possible to carry out a packing operation of the bone replacement material into a vertebral body smoothly, reliably and safely. Further, since the bone replacement material is formed into a pellet having a predetermined shape, a packing operation of the bone replacement material using an inserter can be made easily.

In this case, the roughly polyhedral shape may be any one of a roughly prismatic shape, a roughly hexahedral shape and a roughly rectangular solid a part of which is cut off. This makes it possible to carry out the packing operation of the bone replacement material into a vertebral body more smoothly, reliably and safely. Further, a filling factor of the bone replacement material into a vertebral body can be increased, thereby enabling to exhibit the result of the operation for a long period of time.

Further, in the present invention, it is preferred that each pellet having the roughly polyhedral shape is defined by a plurality of surfaces including a pair of opposite surfaces, in which one of the opposite surfaces is inclined with respect to the other surface at a predetermined angle. In this case, the predetermined angle is preferably in the range of 10 to 60°. Further, in this case, it is also preferred that each pellet of the roughly polyhedral shape is defined by a plurality of edges having different lengths, in which the length of the longest edge is in the range of 5 to 10 mm and/or the length of the shortest edge is in the range of 2 to 5 mm. This also makes it possible to carry out the packing operation of the bone replacement material into a vertebral body more smoothly, reliably and safely. Further, a filling factor of the bone replacement material into a vertebral body can also be increased, thereby enabling to exhibit the result of the operation for a long period of time.

Furthermore, in the present invention, it is also preferred that the volume of each pellet of the bone replacement material is in the range of 13 to 239 mm$^3$. This makes it possible to particularly increase a filling factor of the bone replacement material into a vertebral body while maintaining operability at the time when the bone replacement material is introduced into a vertebral body, thereby enabling to exhibit the result of the operation for a long period of time.

Moreover, in the present invention, it is preferred that each pellet of the bone replacement material has been subjected to a chamfering processing. This makes it possible to prevent the bone replacement material from undesirably damaging anatomy when the packing operation is carried out or the like.

In the present invention, it is also preferred that when the bone replacement material is used for a vertebral body, a number of pellets of the bone replacement material are packed into a cavity of the vertebral body. In this case, the bone replacement material can be introduced into a cavity of the vertebral body using a cylindrical member having a hollow passage. This makes it possible to particularly increase a filling factor of the bone replacement material to a vertebral body, thus enabling to exhibit the result of the operation for a long period of time.

Further, in the present invention, it is also preferred that the bone replacement material is mainly formed of ceramics. In this case, the ceramics is preferably formed of calcium phosphate based compound, and the Ca/P ratio of the calcium phosphate based compound is preferably in the range of 1.0 to 2.0. This makes it possible to improve affinity to living bodies.

These and other objects, structures and advantages of the present invention will be more apparent when the following detailed description of preferred embodiments will be considered in conjunction with the appended drawings.

BRIEF DESCRIPTION OF THE DRAWING

FIGS. 2(A) and (B) are schematic views of a vertebra for explaining a method of packing the bone replacement material into a vertebral body, wherein FIG. 2(A) is a perspective view of a vertebra viewed from the bottom side in which a vertebral body is partially cut away and FIG. 2(B) is a plan view of the vertebra (Note that, in FIG. 3 to FIG. 6 and FIG. 8, the figures (A) and (B) are the same views of FIGS. 2(A) and (B)).

DETAILED DESCRIPTION OF THE PREFERRED EMBODIMENTS

Hereinbelow, preferred embodiments of a bone replacement material according to the present invention will be described in detail with reference to the accompanying drawings.

Figure 1:
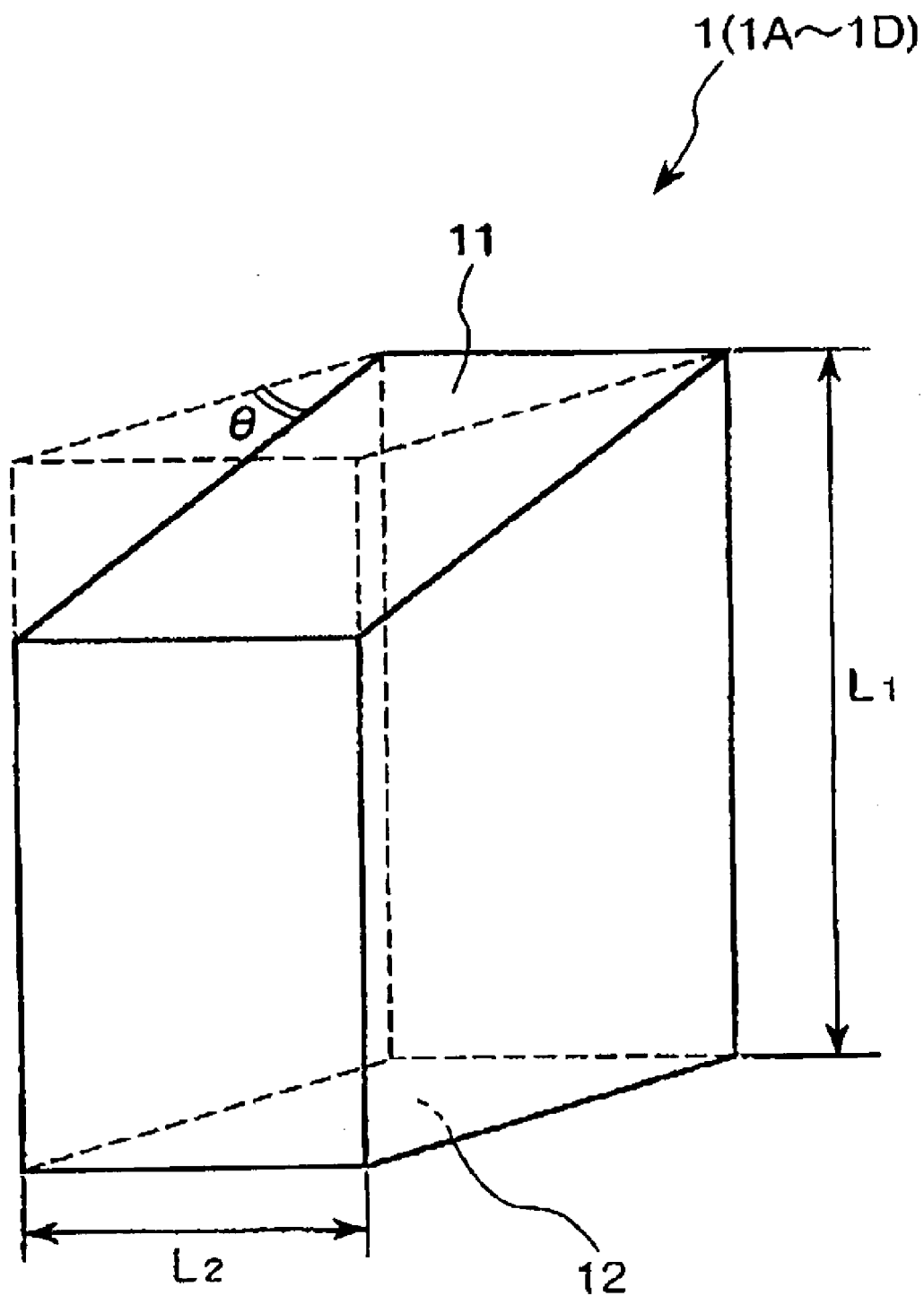
FIG. 1 is a perspective view which shows a preferred embodiment of a bone replacement material according to the present invention.
Figure 2:
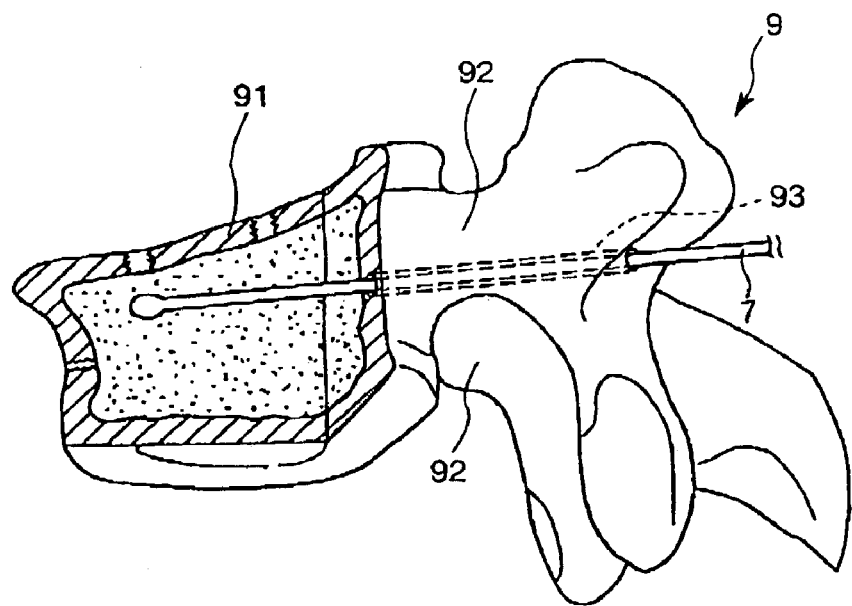
Figure 2:
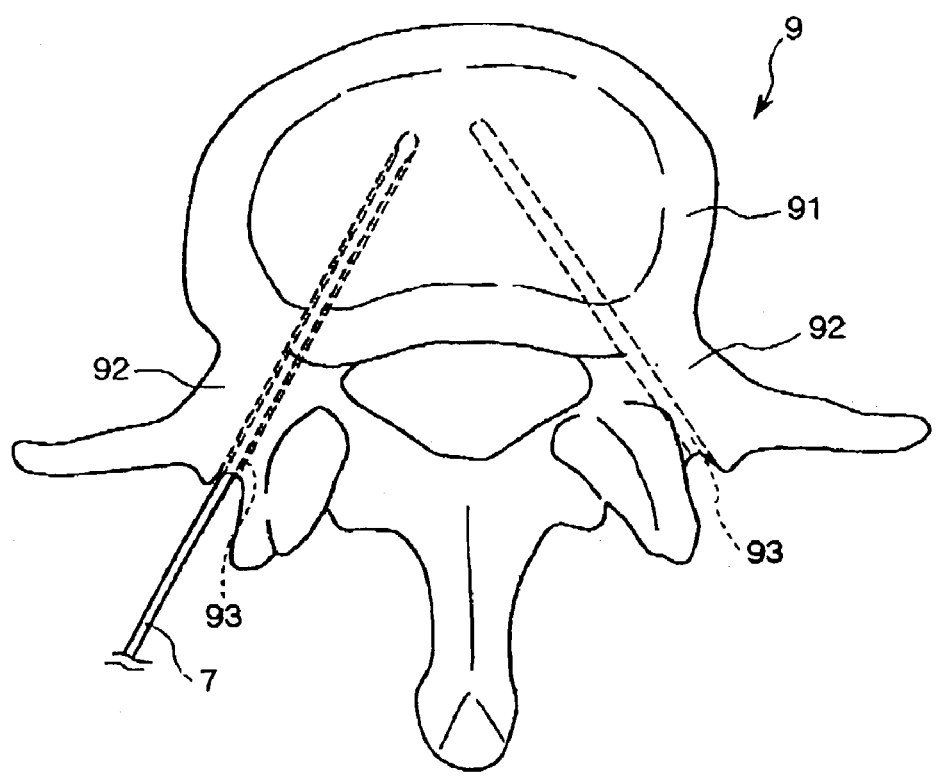
Figure 3:
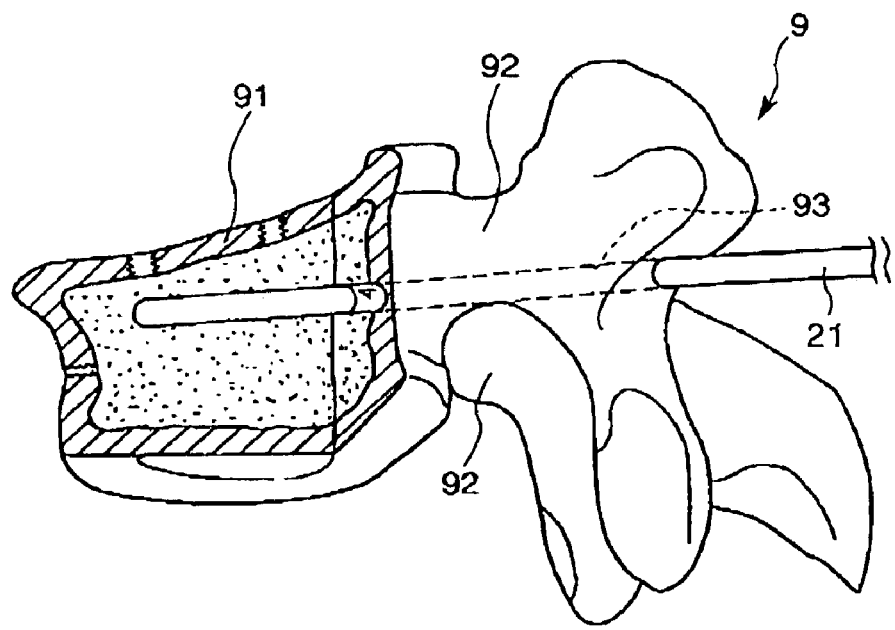
FIGS. 3(A) and (B) are schematic views of the vertebra for explaining the method of packing the bone replacement material into the vertebral body.
Figure 3:
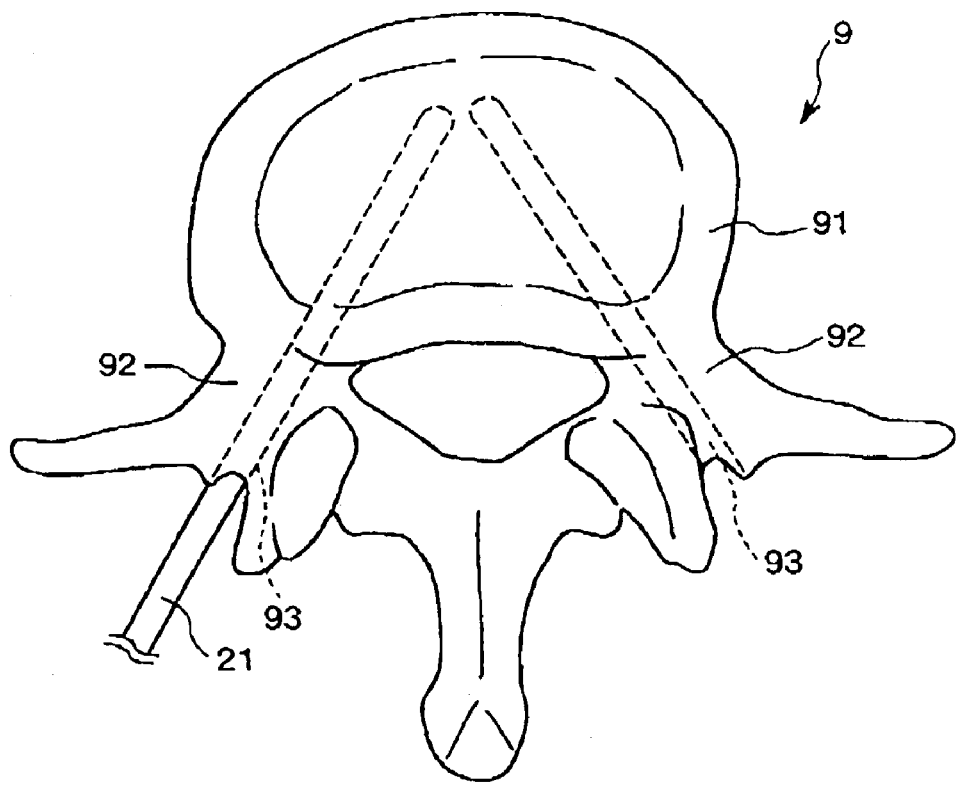

FIG. 1 is a perspective view which shows a preferred embodiment of a bone replacement material according to the present invention. The bone replacement material of the present invention is used for a treatment for repairing or reducing a vertebral body compression fracture, and it is adapted to be packed or inserted into a collapsed vertebral body.

As shown in FIG. 1, the bone replacement material of the present invention 1 (1A, 1B, 1C and 1D) is formed into a pellet or a small block having a roughly polyhedral shape.

In the conventional treatment for repairing a vertebral body compression fracture, a roughly spherical (granular) bone replacement material is used. When such a conventional granular bone replacement material is used, a number of granules are packed within a cavity of a vertebral body in a state that each granule is in contact with adjacent other granules through small contacting areas due to its spherical shape. Therefore, the packed granules are in an unstable state within the vertebral body, thus displacement is likely to occur when a load is applied. When such displacement of the granules occurs, density of the packed bone replacement material becomes uniform at various positions inside the vertebral body. In other words, the cavity of the vertebral body will have a portion where an amount of the packed bone replacement material is insufficient. As a result, the volume of the vertebral body is decreased due to a load applied thereto, so that there is a case that the result of the operation can not be obtained sufficiently.

In contrast with the conventional bone replacement material descried above, the bone replacement material of the present invention is formed into a pellet or small block having a roughly polyhedral shape, such a problem as involved in the conventional bone replacement material will be hard to occur. Specifically, according to the present invention, adjacent bone replacement materials 1 are in surface to surface contact with each other so that they are held or fixated stably. This realizes a load withstanding capacity. Therefore, even when the bone replacement material is used in a site where a load is applied, satisfactory packing condition can be maintained inside the cavity of the vertebral body without displacement for a long period of time.

As can be seen in FIG. 1, the roughly-polyhedral pellets are each formed as a solid and free of any through hole being provided therethrough.

Further, by forming the bone replacement material into a pellet having a roughly polyhedral shape, it becomes possible to increase the filling factor in the cavity of the vertebral body, that is to reduce the space occupied by gaps. This makes it possible to suppress reduction in the volume of the vertebral body after operation, so that it becomes possible to maintain the result of the operation for a long period of time.

Furthermore, by forming the bone displacement material into a pellet having such a shape as mentioned above, it also becomes possible to effectively avoid an undesirable situation that the bone displacement material remains near an opening of a cylindrical member 51 which is described later. This makes it possible to pack a sufficient amount of the bone replacement material into a cavity of a vertebral body.

Further, when this bone displacement material is used, there is less possibility that the hollow inner passage of the cylindrical member will be clogged with the bone replacement material, so that a packing operation of the bone replacement materials can be carried out smoothly and reliably.

The pellet-type bone displacement material of the present invention can have various shapes so long as they have a roughly polyhedral shape. However, preferably, the bone replacement material is formed into a pellet having a roughly prismatic shape (a part of which may be removed or cut off), more preferably, it is formed into a pellet having a roughly hexahedral shape (a part of which may be removed or cut off), and even more preferably, it is formed into a pellet a roughly rectangular solid (a part of which may be removed or cut off). If the bone replacement material of the present invention is formed into a pellet having any one of the above mentioned shapes, the results stated above will become more conspicuous.

Further, in the present invention, it is preferred that the bone replacement material is formed into a pellet having a roughly polyhedral shape which is defined by a plurality of surfaces including a pair of opposite surfaces, in which one of the opposite surfaces is inclined with respect to the other surface at a predetermined angle as shown in FIG. 1. As will be described later in more detail, if each pallet of the bone replacement material is formed into a shape having such inclined opposite surfaces, the pellets of the bone replacement material 1 are dispersed inside a cavity of a vertebral body effectively when they are packed into the cavity, thereby enabling to further increase the filling factor of the bone replacement material 1. The embodiment shown in FIG. 1 is an example of a pellet of the bone replacement material 1. As shown in the drawing, the pellet of the bone replacement material 1 is formed into a roughly rectangular solid in which a part thereof is removed or cut off so that one of the opposite surfaces 11 is inclined with respect to the other surface 12 at an angle $\theta$.

The above-mentioned angle $\theta$ is preferably in the range of 10 to 60°, and more preferably in the range of 20 to 40°. If the angle $\theta$ is smaller than the lower limit value, there is a case that the effect obtained by the inclined surfaces can not be exhibited sufficiently. On the other hand, if the angle $\theta$ is larger than the upper limit value, sharp protrusions are formed on the bone replacement material so that clacking is likely to occur when a load is applied thereto.

Further, in the bone replacement material of the present invention, the length $L_1$ of the longest edge of each pellet is preferably in the range of 5 to 10 mm, and more preferably in the range of 5 to 7 mm. If the length $L_1$ of the longest edge is shorter than the lower limit value, a volume of each pellet of the bone replacement material becomes small, thus load withstanding capacity is lowered. On the other hand, the length $L_1$ of the longest edge is longer than the upper limit value, desirable dispersion of the bone replacement material 1 is not likely to occur in the vertebral body.

Furthermore, in the bone replacement material of the present invention, the length $L_2$ of the shortest edge of each pellet is preferably in the range of 2 to 5 mm, and more preferably in the range of 3 to 4 mm. If the length $L_2$ of the shortest edge is shorter than the lower limit value, a volume of each pellet of the bone replacement material becomes small, thus load withstanding capacity is lowered. On the other hand, the length $L_2$ of the shortest edge is longer than the upper limit value, packing operation through a vertebral arch becomes difficult.

Moreover, in the present invention, the volume of each pellet of the bone replacement material is preferably in the range of 13 to 239 mm$^3$, and more preferably in the range of 40 to 100 mm$^3$. If the volume of each pellet of the bone replacement material is smaller than the lower limit value, the volume of each pellet of the bone replacement material becomes too small, thus load withstanding capacity also is lowered. On the other hand, if the volume of each pellet of the bone replacement material is larger than the upper limit value, desirable dispersion is not likely to occur in the vertebral body.

The bone replacement material 1 of the present invention may be comprised of various pellets having different sizes depending on cases (patient shapes).

Further, in the bone replacement material 1 of the present invention, it is preferred that each pellet is subjected to chamfering processing. By subjecting each pellet to chamfering processing, it is possible to prevent the bone replacement material 1 from undesirably damaging anatomy when the packing operation is carried out or in a state that a vertebral body is filled with the bone replacement material 1.

Further, the bone replacement material 1 of the present invention is preferably formed of a material that can be used as a biomaterial. The manufacturing method of the bone replacement material is not particularly limited to any specific one.

Examples of materials that can be used for the biomaterial include various kinds of ceramics such as alumina, zirconia, calcium phosphate-based compound, and the like. Among these materials, calcium phosphate-based compound is preferable. This is because, since a calcium phosphate-based compound remains stably in a living body over a long period of time, it is particularly suitable for use as a biomaterial.

Examples of the calcium phosphate-based compound include hydroxy apatite $(Ca_{10}(PO_4)_6(OH)_2)$, TCP $(Ca_3(PO_4)_2)$, $Ca_2P_2O_7$, $Ca(PO_3)_2$, $Ca_{10}(PO_4)_6F_2$, $Ca_{10}(PO_4)_6Cl_2$, DCPD$(CaHPO_4 \cdot 2H_2O)$, $Ca_4O(PO_4)_2$, and the like, and one kind of or a mixture of two or more kinds of these calcium phosphate-based compounds may be employed.

In particular, a calcium phosphate-based compound having a Ca/P ratio of 1.0–2.0 is preferably used. By setting the Ca/P ratio to 1.0–2.0, the bone replacement material can have a Ca/P ratio closer to that of a bone tissue of a living body, so that it is being existed inside the living body for a long period of time.

Hereinafter, a description will be made with regard to one example of the method for packing the bone replacement material 1 of the present invention into a vertebral body.

FIGS. 2 to 8 are schematic views for explaining the method for packing or Introducing the bone replacement material 1 of the present invention. Further, FIG. 9 is a schematic view showing a vertebral body to which a treatment for repairing a vertebral body compression fracture has been carried out. FIGS. 10 to 14 show examples of surgical instruments used for the treatment for repairing a vertebral body compression fracture including an packing operation of the bone replacement material 1. However, it is to be noted that the surgical instruments that can be used for the treatment are not limited to the instruments shown in these drawings.

In connection with the drawings, it is to be noted that FIGS. 2(A) to 6(A) and FIG. 8(A) are perspective views of a vertebra viewed from the bottom thereof, in which a vertebral body is partially cut away, and FIGS. 2(B) to 6(B) and FIG. 8(B) are plan views of the vertebra. Hereinafter, in relation to FIGS. 2(A) to 6(A) and FIG. 8(A), the left side and the right side will be referred to as the "distal end" and the "proximal end" respectively. Also, in relation to FIGS. 2(A) to 6(A) and FIG. 8(A), the upper side and the lower side will be referred to as the "upper side (head side)" and the "lower side (leg side)", respectively; and the left side and the right side will be referred to as the "anterior side (ventral side)" and the "posterior side (dorsal side)", respectively.

<1> First, as shown in FIGS. 2(A) and 2(B), under X-ray guidance, a probe (a surgical instrument) 7 is pierced or inserted via each vertebral arch 92, 92 toward the targeted vertebral body 91 on each side of the vertebra 9 to which a treatment for repairing vertebral body compression fracture is carried out. Consequently, on either side of the vertebra 9, paths 93, 93 are formed so as to pass though the vertebral arch 92 into the vertebral body 91. Each of the paths 93, 93 has a small diameter.

Figure 10:
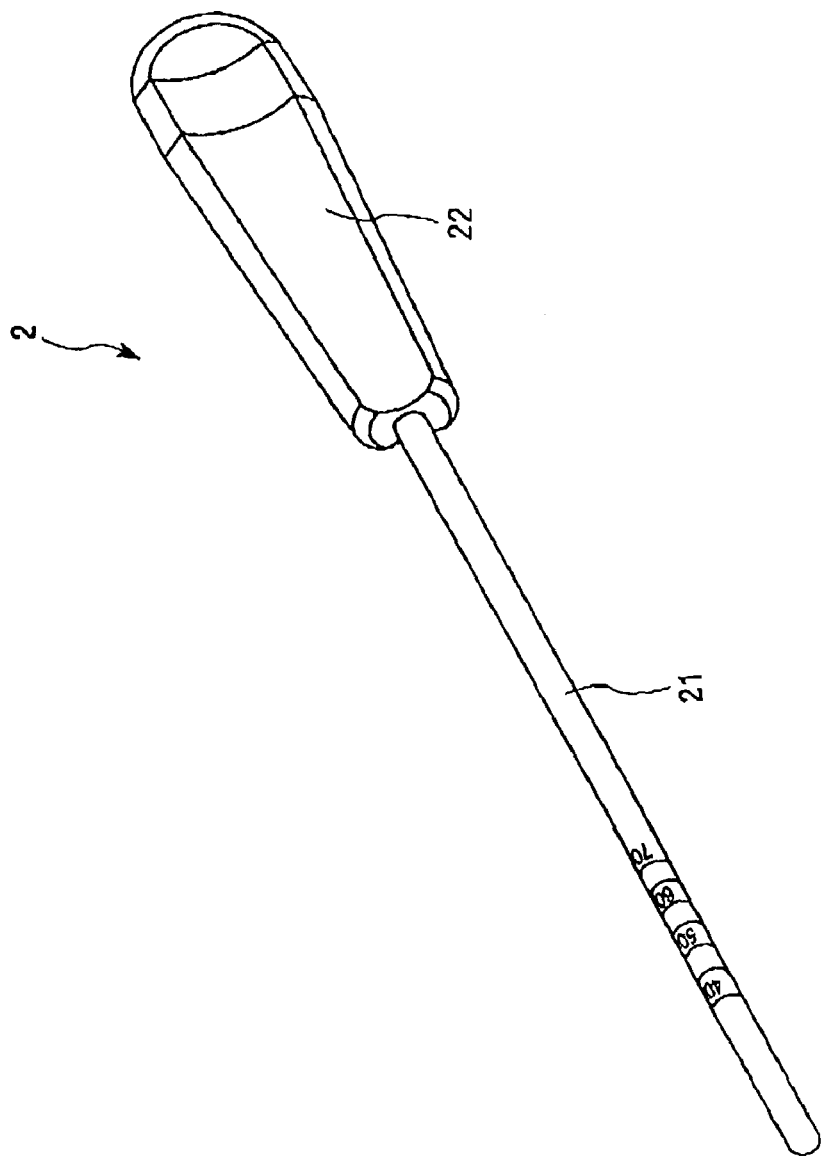
FIG. 10 is a perspective view which shows an example of a guide rod used for the treatment.

<2> Next, using a guide rod 2, the diameter of the path 93 is widened. As shown in FIGS. 3(A) and 3(B) and FIG. 10, the guide rod 2 includes a rod-shaped portion 21 and a grip portion 22 mounted to a proximal end of the rod-shaped portion 21.

As shown in FIGS. 3(A) and 3(B), an operator grips the grip portion 22 of the guide rod 2, and then insert the distal end of the rod-shaped portion 21 into one of the paths 93, 93. In this way, the path 93 is widened.

In this regard, it is to be noted that two or more guide rods 2 are prepared, in which each rod-shaped portion 21 has a different outer diameter (e.g., three types of guide rods having an outer diameter of 4 mm, 5 mm, and 6 mm, respectively). By using these guide rods 2 in the order in which the outer diameter is increased, it is possible to widen the path 93 in multiple steps. Such an operation is performed on each of the paths 93 on the right and left sides.

<3> Next, using a vertical elevator 3, an upper portion of the vertebral body 91, in particular an upper anterior surface of the inside of the vertebral body 91 is returned (reduced) to a substantially normal position.

Figure 4:
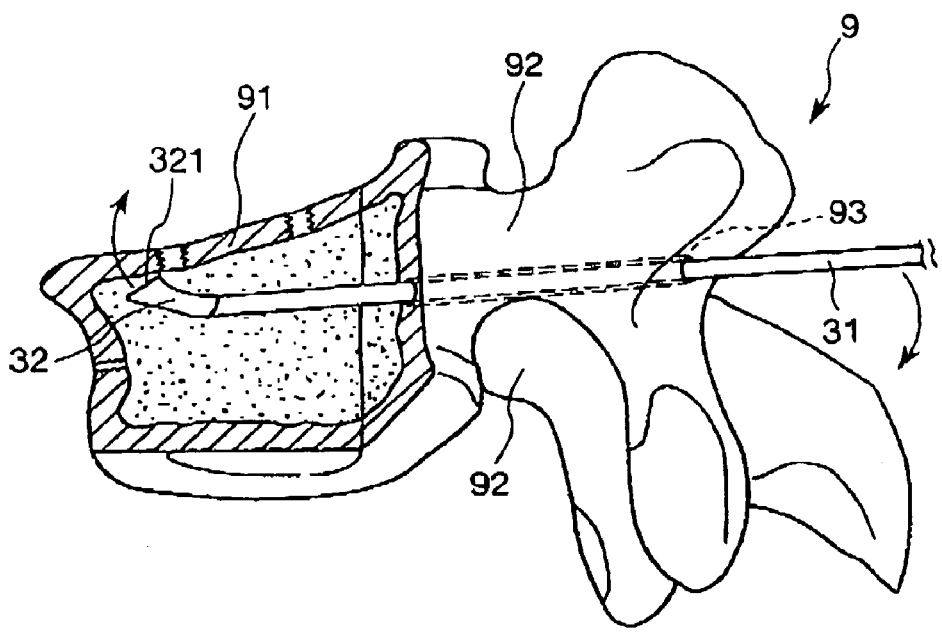
FIGS. 4(A) and (B) are schematic views of the vertebra for explaining the method of packing the bone replacement material into the vertebral body.
Figure 4:
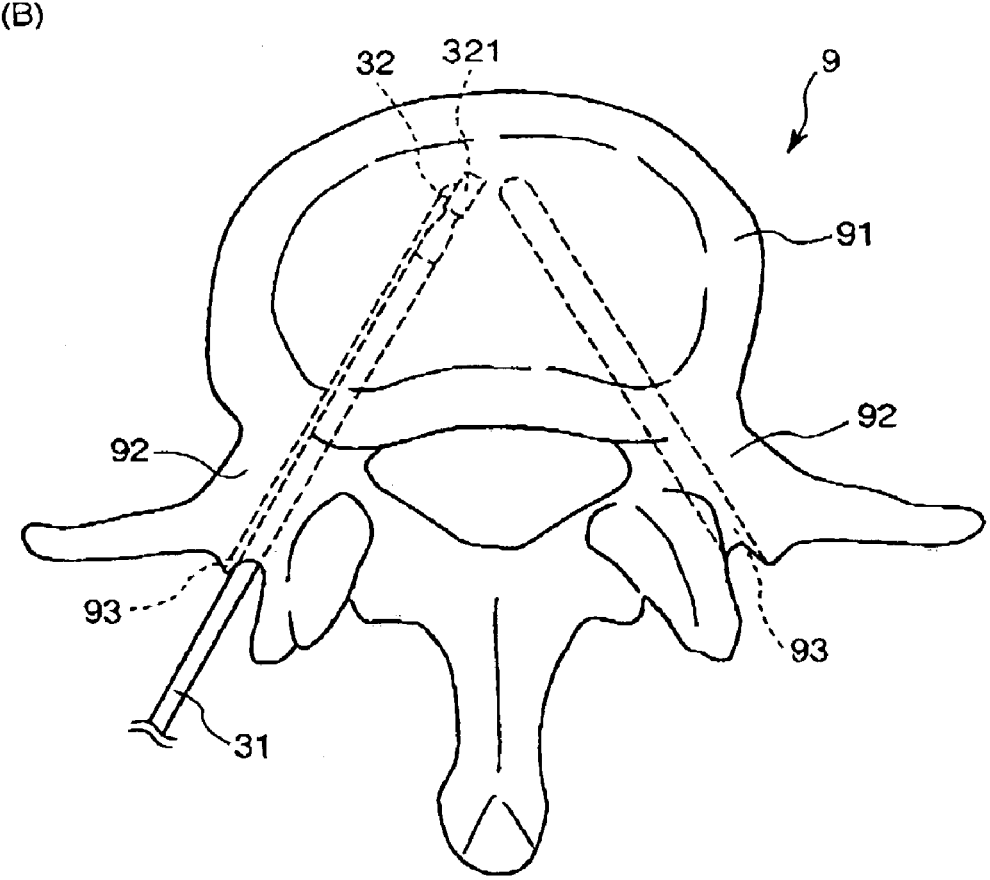
Figure 11:
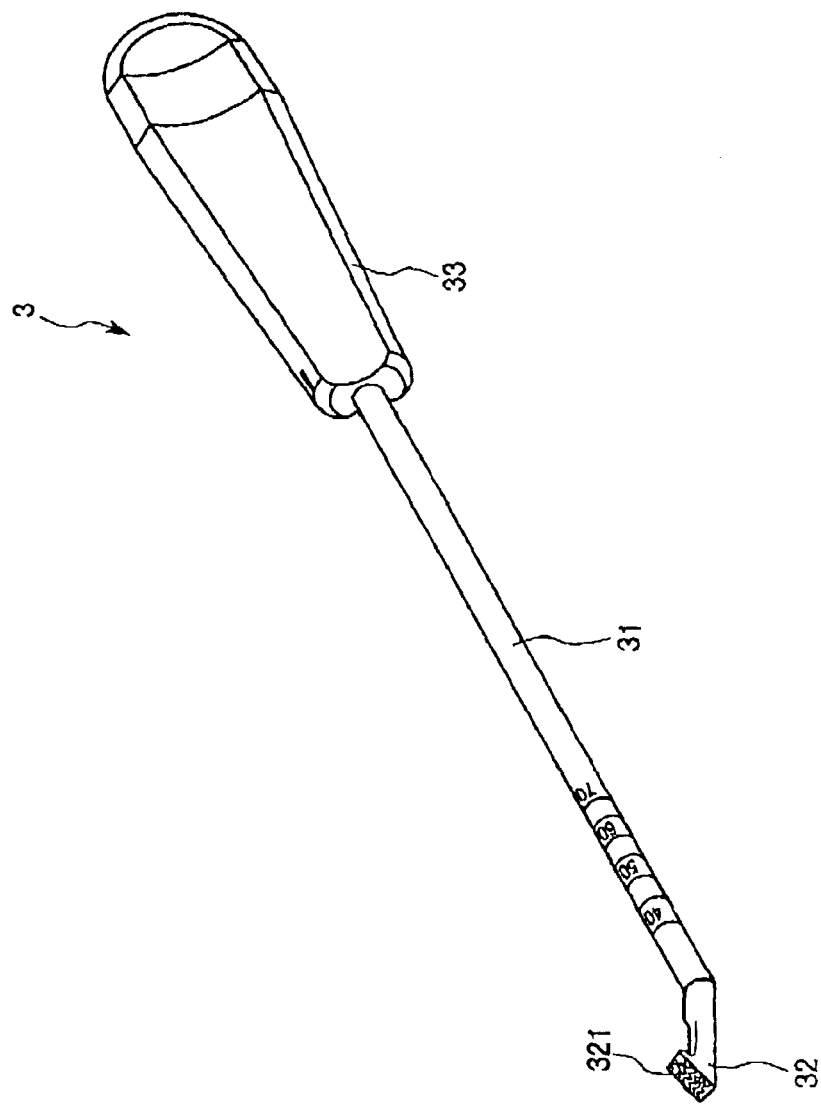
FIG. 11 is a perspective view which shows an example of a vertical elevator used for the treatment.

As shown in FIGS. 4 and 11, the vertical elevator 3 includes a rod-shaped main body 31, a pushing portion 32 provided on the distal end of the rod-shaped main body 31 and a grip portion 33 provided on the proximal end of the rod-shaped main body 31.

As shown in FIG. 4, the operator grips the grip portion 33 of the vertical elevator 3 to insert the distal end portion of the vertical elevator 3, including the pushing portion 32 and the distal end portion of the main body 31, into the vertebral body 91 through one of the paths 93 to position the pushing portion 32 in the anterior portion of the vertebral body 91. At this time, the distal end surface 321 of the pushing portion 32 is set so as to point in an upward direction.

Then, the proximal end portion of the main body 31 is pushed downwardly so that the distal end surface 321 of the pushing portion 32 comes into contact with the upper anterior surface of the inside of the vertebral body 91 and then the upper anterior portion of the vertebral body 91 is pushed upwardly. Consequently, the upper anterior portion of the vertebral body 91 is upwardly elevated.

When such an operation is complete, the distal end portion of the vertical elevator 3 is removed from the vertebra 9, and then the operator again inserts the vertical elevator 3 into the vertebral body 91 through the other path 93 to perform the same operation as described above.

<4> Next, using a horizontal elevator 4, an upper portion of a vertebra 91, in particular the upper middle portion of the inside of the vertebral body 91 is returned (reduced) to its normal position.

Figure 5:
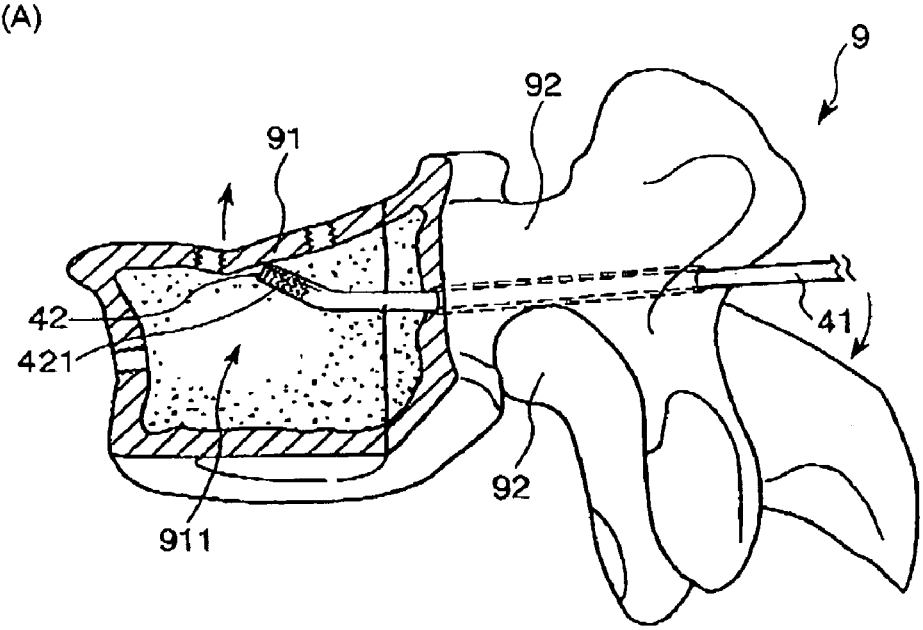
FIGS. 5(A) and (B) are schematic views of the vertebra for explaining the method of packing the bone replacement material into the vertebral body.
Figure 5:
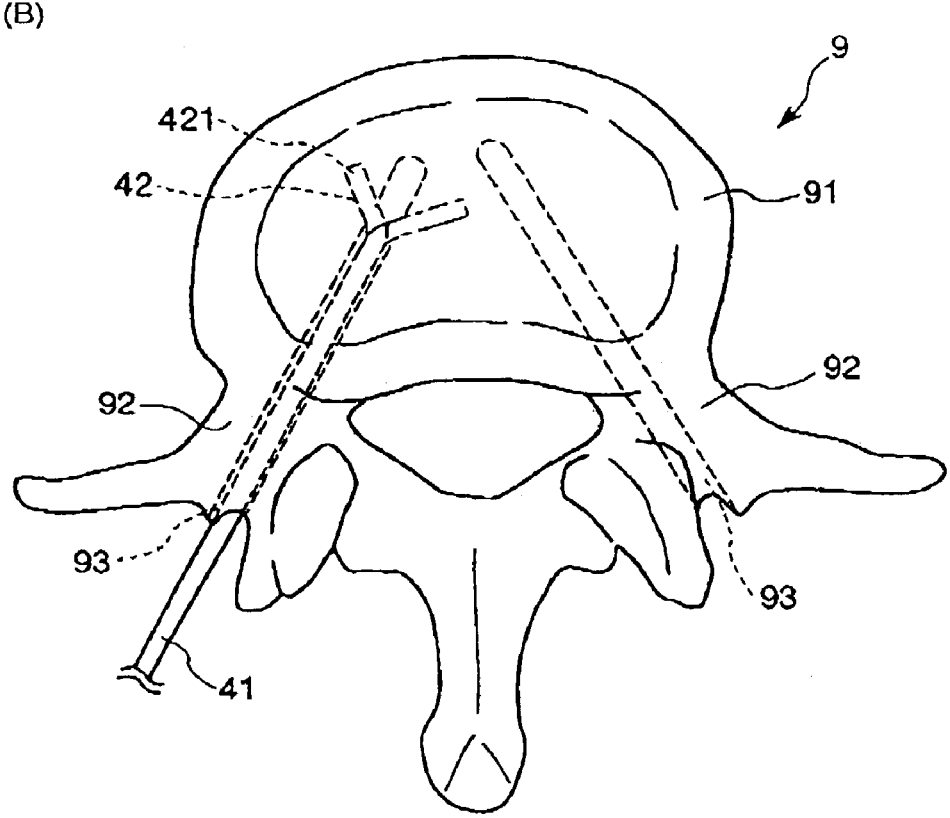
Figure 12:
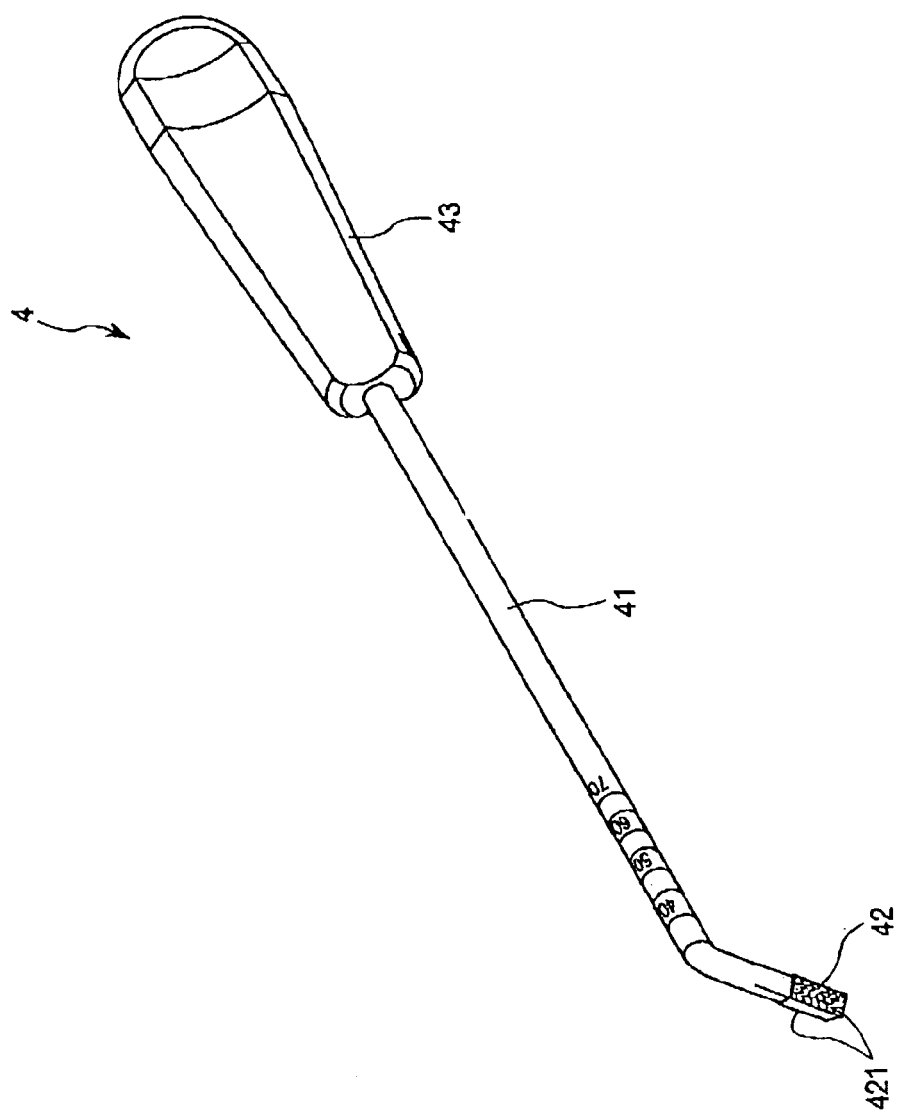
FIG. 12 is a perspective view which shows an example of a horizontal elevator used for the treatment.

As shown in FIGS. 5 and 12, the horizontal elevator 4 includes a rod-shaped main body 41, a pushing portion 42 provided on the distal end of the main body 41 and a grip portion 43 provided on the proximal end of the rod-shaped main body 41.

As shown in FIG. 5, the operator grips the grip portion 43 of the horizontal elevator 4 to insert the distal end portion of the horizontal elevator 4, including the pushing portion 42 and the distal end portion of the main body 41, into the vertebral body 91 through one of the paths 93 to position the pushing portion 42 in the middle portion of the vertebral body 91. At this time, one of the side surfaces 421 of the pushing portion 42 is set so as to point in an upward direction.

Then, the proximal end of the main body 41 is pushed downwardly so that the side surface 421 of the pushing portion 42 comes into contact with the upper middle surface of the inside of the vertebral body 91 and then the upper middle portion of the vertebral body 91 is pushed upwardly. Consequently, the upper middle portion of the vertebral body 91 is upwardly elevated.

Further, the pushing portion 42 is turned about an axis of the main body 41 by a prescribed angle, and then the same operation as described above is performed. In this way, it is possible to perform the reduction procedure on the upper middle portion of the vertebral body 91 over a wide range.

When such an operation is complete, the distal end portion of the horizontal elevator 4 is removed from the vertebra 9. Further, the operator again inserts the horizontal elevator 4 into the vertebral body 91 through the other path 93 to perform the same procedures as described above.

Each of the reduction procedures described in <3> and <4> is repeatedly performed two or more times until the vertebral body 91 is returned to a substantially normal shape.

In this regard, it is to be noted that the cavity 911 is created within the vertebral body 91 as a result of the reduction procedures mentioned above.

<5> Next, using an inserter (packing instrument) 5, a bone displacement material 1 in the form of a pellet is packed into the inside of the vertebra 91 of which shape has been returned to its original shape (that is, into the cavity 911 formed inside the vertebral 911 by the reduction procedure).

Figure 6:
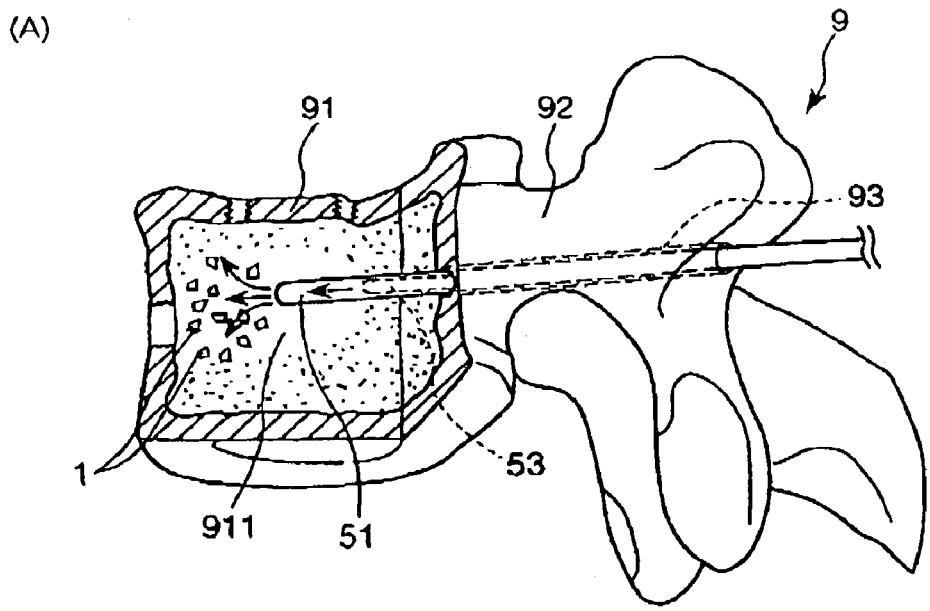
FIGS. 6(A) and (B) are schematic views of the vertebra for explaining the method of packing the bone replacement material into the vertebral body.
Figure 6:
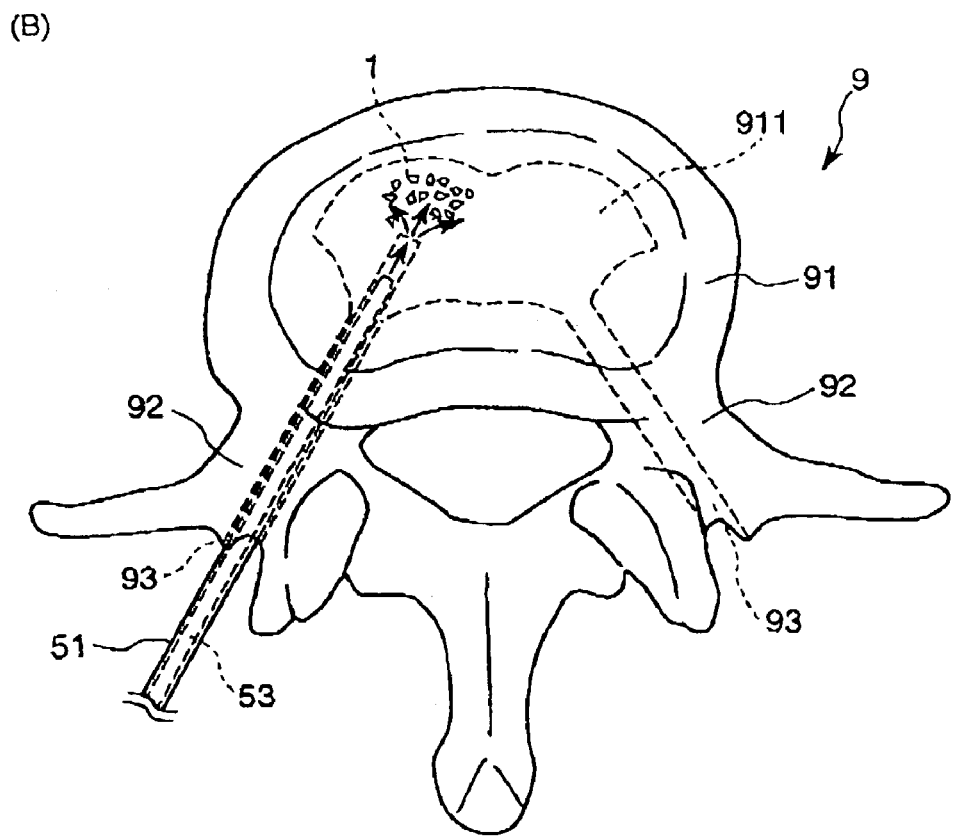
Figure 13:
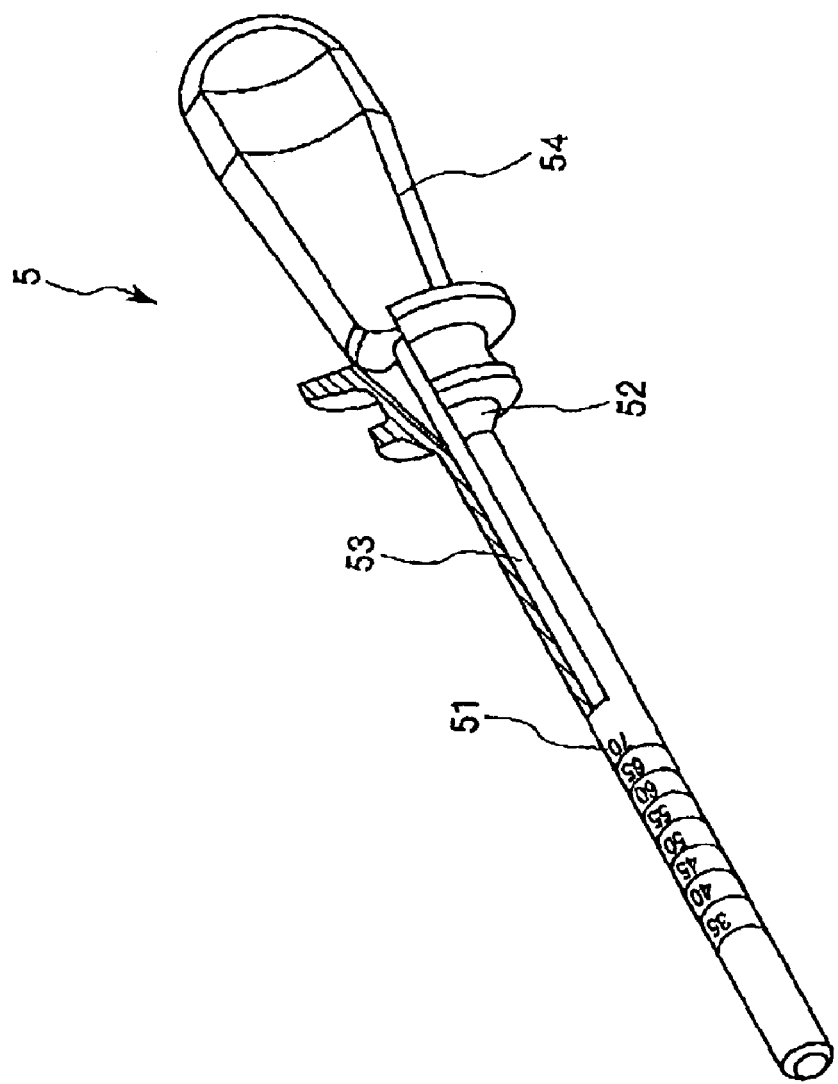
FIG. 13 is a perspective view which shows an example of an inserter used for the treatment.

As shown in FIGS. 6 and 13, the inserter 5 includes a cylindrical member 51, an ejector bar 53 adapted to be inserted into a hollow passage of the cylindrical member 51, a cylindrical member grip portion 52 provided on the proximal end of the cylindrical member 51, and an ejector bar grip portion 54 provided on the proximal end of the ejector bar 53.

As shown in FIG. 6, the operator grips the cylindrical member grip portion 52 of the cylindrical member 51 of the inserter 5 to insert the distal end portion of the cylindrical member 51 into the vertebral body 91 through one of the paths 93, so that the distal end of the cylindrical member 51 is positioned at a desired position within the cavity 911.

While the operator maintains grip on the cylindrical member grip portion 52 with one hand to maintain the position of the distal end of the cylindrical member 51 within the vertebral body 91, a number of pellets of the bone replacement material 1 are fed into the passage of the cylindrical member 51 from the proximal end of the cylindrical member grip portion 52.

Then, the operator grips the ejector bar grip portion 54 of the ejector bar 53 with the other hand to insert the ejector bar 53 into the passage of the cylindrical member 51 from the proximal end of the cylindrical member grip portion 52 toward the distal end of the cylindrical member 51. By doing so, the pellets of the bone replacement material 1 placed in the passage of the cylindrical member 51 are pushed by the distal end of the ejector bar 53 toward the distal end of the cylindrical member 51.

By further pushing the ejector bar 53 toward the distal end of the cylindrical member 51, the distal end of the ejector bar 53 projects out of the distal end of the cylindrical member 51 so that the pellets of the bone replacement material are successively introduced into the cavity 91 and the cavity is filled with the pellets of the bone replacement material.

In this case, the bone replacement material 1 of the present invention is formed into a pellet having the above mentioned shape, packing operation thereof into the vertebral body can be carried out smoothly, reliably and safely. In particular, in this embodiment, each pellet of the bone replacement material 1 has the shape having an inclined surface as described above. Therefore, when the bone replacement material 1 is packed into the cavity 91 using the cylindrical member 51, the pellets of the bone replacement material 1 are pushed by the ejector bar 53 so that each pellet of the bone replacement material 1 is pushed out in a predetermined direction along the inclined surface of the adjacent pellet of the bone replacement material 1.

Figure 7:
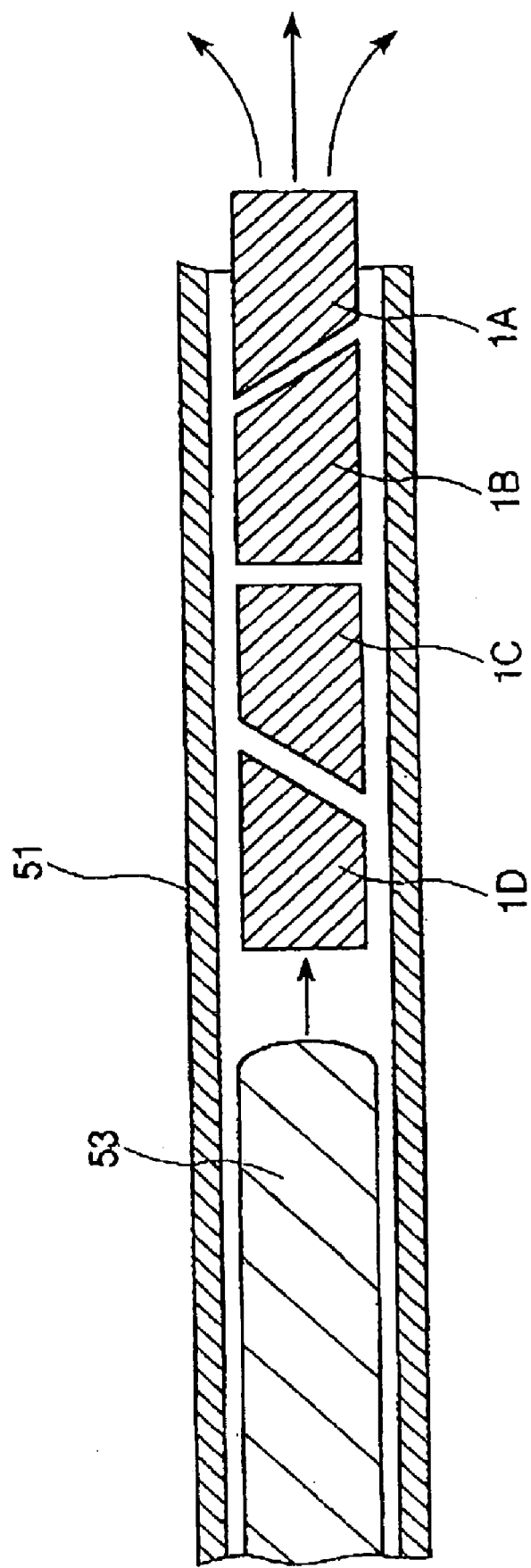
FIG. 7 is a cross sectional view of a cylindrical member in which a plurality of pellets of the bone replacement material are placed.

In more details, in the example shown in FIG. 7, the pellet 1A of the bone replacement material is pushed out upwardly in the drawing by the inclined surface of the adjacent pellet 1B. The pellet 1B of the bone replacement material is pushed out in a direction substantially parallel to the cylindrical member 51. Further, the pellet of the bone replacement material 1C is pushed out downwardly in the drawing by the adjacent pellet of the bone replacement material 1D.

Further, since the bone replacement material 1 has the shape as described above, when a plurality of pellets of the bone replacement material 1 are successively introduced into the vertebral body, the introduced pellets of the bone replacement material 1 are dispersed into various directions, thereby making it possible that the cavity 911 is filled with the pellets of the bone replacement material 1 uniformly. Further, since the bone displacement material that has been introduced into the cavity 911 does not remain near the opening of the cylindrical member 51, it is possible to pack a sufficient amount of the pellet-type bone replacement material 1.

Furthermore, since it is possible to prevent the hollow passage of the cylindrical member 51 from being clogged with the bone replacement material, it is possible to carry out the packing operation smoothly and reliably.

In this packing operation for packing the pellets of the bone replacement material 1 into the cavity 911, the maximum length of the ejector bar 53 projecting out from the distal end of the cylindrical member 51 is limited due to the abutment of the ejector bar grip portion 54 with the cylindrical member grip portion 52. Therefore, it is possible to prevent the ejector bar 53 from projecting out more than a necessary amount, thereby preventing the ejector bar 53 from involuntarily pushing the vertebral body 91, thus providing a high level of safety.

<6> Next, using an impactor 6, the density of the bone replacement material packed in the vertebral body 91 which has been reduced is increased.

Figure 8:
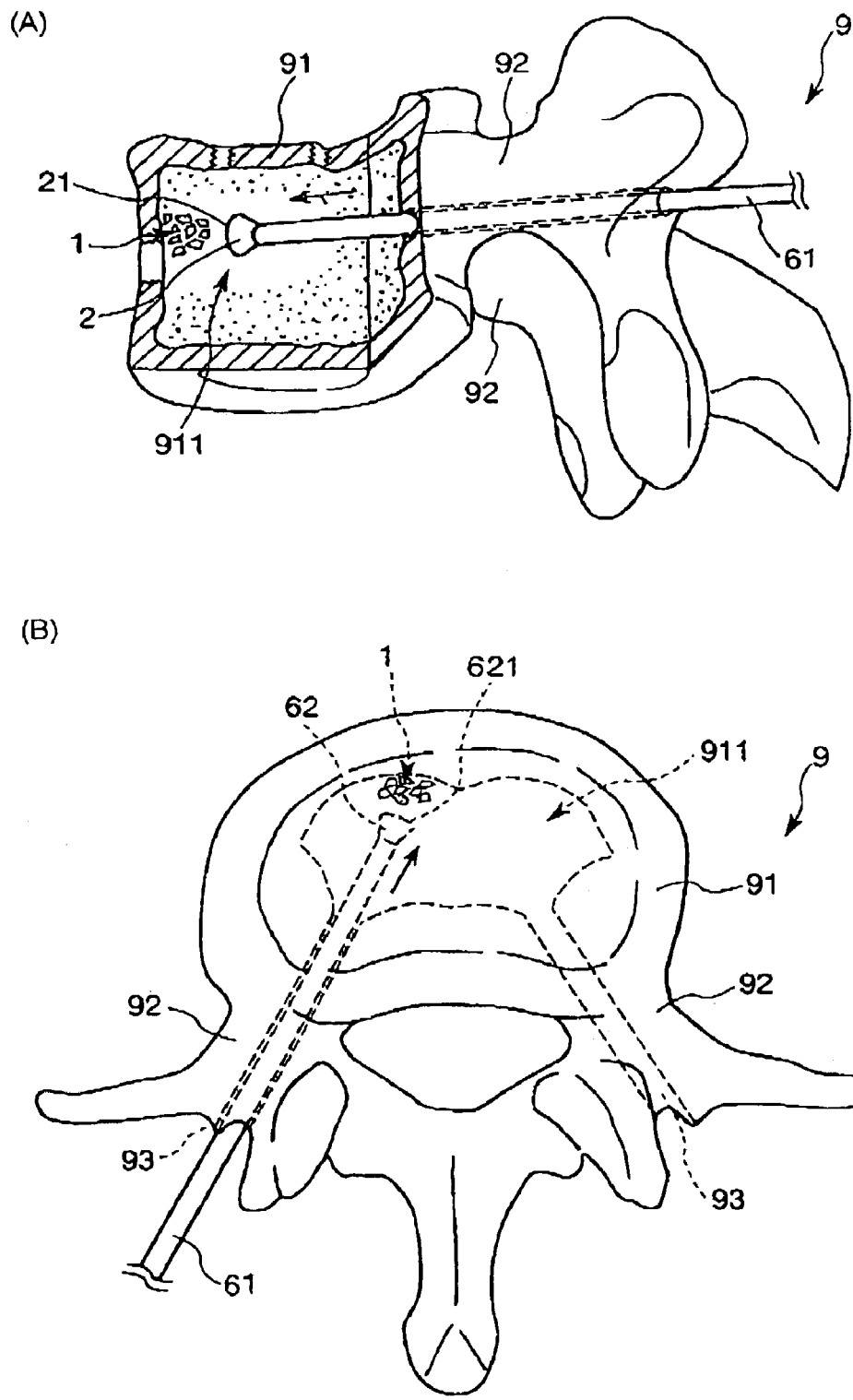
FIGS. 8(A) and (B) are schematic views of the vertebra for explaining the method of packing the bone replacement material into the vertebral body.
Figure 9:
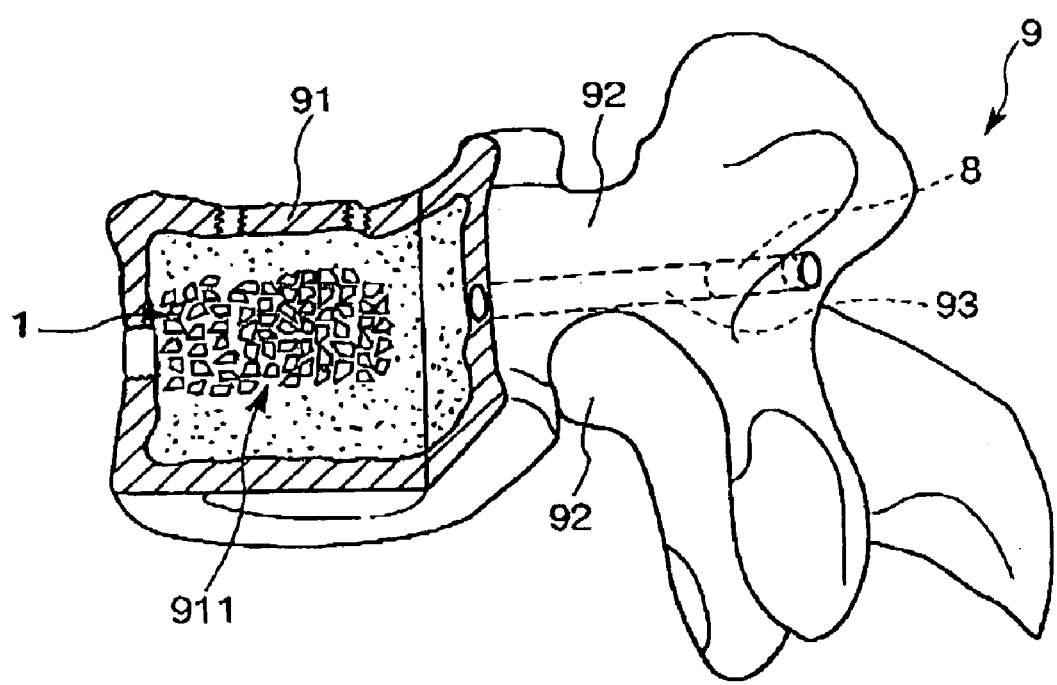
FIG. 9 is a schematic view of the vertebra to which the treatment for repairing a vertebral body compression fracture has been carried out using the bone replacement material according to the present invention.
Figure 14:
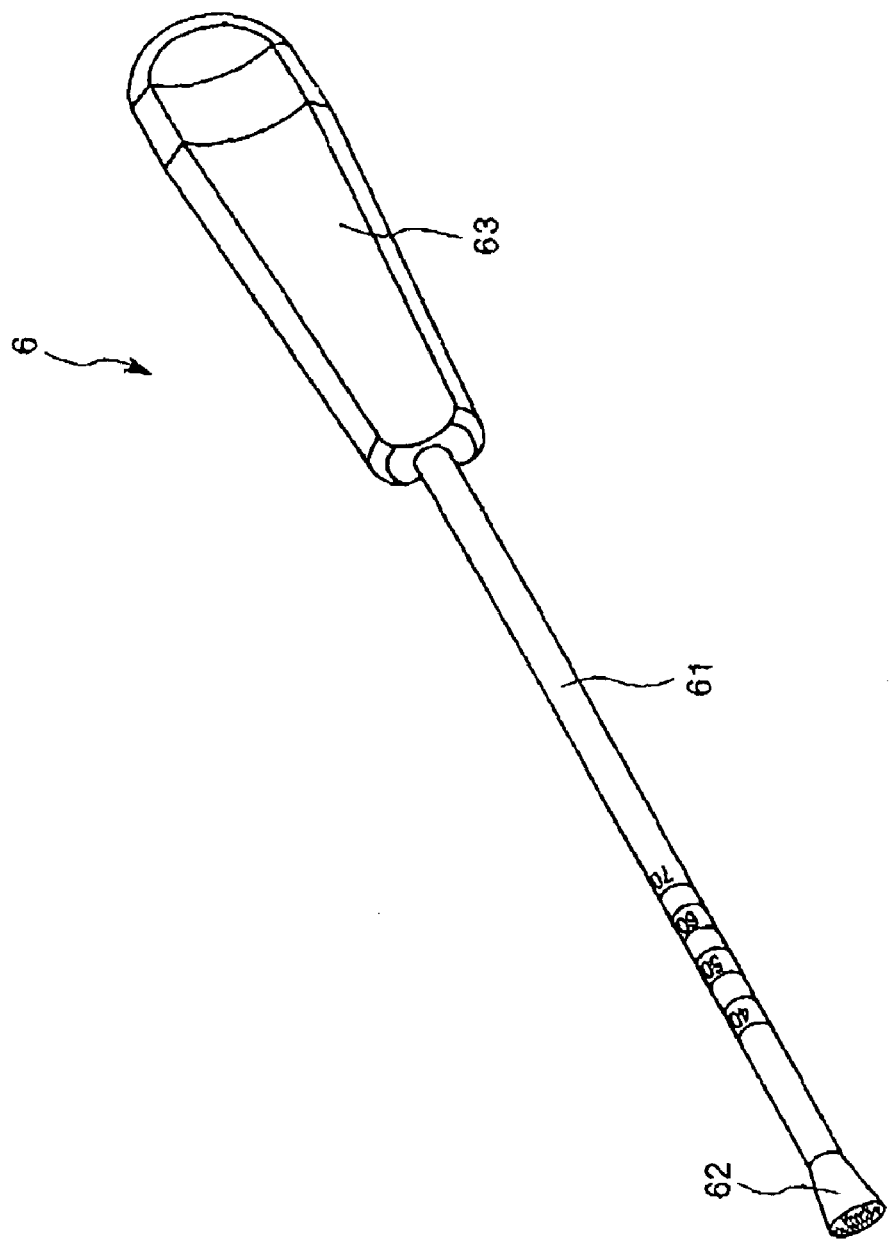
FIG. 14 is a perspective view which shows an example of an impactor used for the treatment.

As shown in FIGS. 8 and 14, the impactor 6 includes a rod-shaped main body 61, an impacting portion 62 provided on the distal end of the rod-shaped main body 61 and a grip portion 63 provided on the proximal end of the rod-shaped main body 61.

As shown in FIG. 8, the operator grips the grip portion 63 of the impactor 6 to insert the distal end portion of the impactor 6, including the impacting portion 62 and the distal end portion of the main body 61, into the vertebral body 91 through one of the path 93.

Then, the pallets of the bone replacement material 1 introduced in the cavity 911 by the operation described in <5> are impacted by the impacting portion 62, thereby increasing the density (filling density) of the bone replacement material 1.

By repeatedly performing each of the operation for packing the bone replacement material 1 described in <5> and the operation for increasing the density of the bone replacement material 1 described in <6> two or more times through each of the paths 93 on the right and left sides, the cavity 911 created in the vertebral body 91 is filled with the bone replacement material 1 and its filling density is also increased. In this case, by using the pellet-type bone replacement material 1 having the inclined surface 11, this density increasing process can be more effectively carried out. This is because when the pellet-type bone replacement material is impacted by the impactor 6, the pellets of the bone replacement material 1 are pushed into a space in the cavity 911 with sliding each other at their inclined surfaces 11, thereby the cavity 911 is filled with the pellets of the bone replacement material 1 so as to have a high filling density.

By performing such operations described in <5> and <6>, the vertebral body 91 may be further reduced.

<7> Next, as shown in FIG. 9, each of the paths 93 on the right and left sides is sealed with a plug 8 made of a biomaterial such as hydroxyapatite or the like. By doing so, it is possible to prevent the bone replacement material 1 from leaking out of the inside of the vertebral body 91 (cavity 911) through the paths 93, 93. Therefore, it is possible to prevent the vertebral body 91 from being collapsed again.

In this regard, it is to be noted that each of the paths 93 is sealed with, for example, a bone cement or the like instead of the plug 8.

Once all of the surgical procedures for the treatment of a compression fracture of the vertebral body 91 are complete, the operation site (incision site) is closed by suturing or ligation to finish the surgical operation.

As described above, each pellet of the bone replacement material 1 packed in the vertebral body has a roughly polyhedral shape, the pellets of the bone replacement material 1 are in surface to surface contact with each other so that they are stably fixated with this result, a load withstanding capacity can be secured, and therefore if the bone replacement material 1 is used at a site where a load is likely to be applied, displacement of the pellets will hardly occur, so that satisfactory packing condition can be maintained.

Further, according to the bone replacement material of the present invention, the cavity of the vertebral body can be filled without any space or gap, it is possible to suppress the decrease of the volume of the vertebral body after the operation, thereby enabling to maintain the result of the operation for a long period of time.

In the foregoing, the description was made with regard to the bone replacement material of the present invention based on the embodiment shown in the drawings. However, it should be understood that the present invention is not limited to the embodiment.

As described above, according to the present invention, the packing operation of the bone replacement material can be carried out smoothly, reliably and safely.

Further, according to the present invention, it is possible to pack the bone replacement material to all portions of the inside of the vertebral body (cavity) uniformly and sufficiently.

Furthermore, according to the present invention, since satisfactory packing condition can be maintained inside the vertebral body, it is possible to maintain the result of the operation for a long period of time.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2002-171814 (filed on Jun. 12, 2002) which is expressly incorporated herein by reference in its entireties.

What is claimed is:

1. A bone replacement, comprising:
a plurality of bone-replacement pellets configured to be introduced into a hollow passage of an instrument that introduces the pellets into a cavity of a vertebral body, each pellet being defined by a plurality of surfaces including a pair of opposite non-adjoined surfaces that are inclined with respect to each other at a predetermined angle, and an inclined surface of a first pellet facing an adjacent second pellet when the pellets are introduced into the hollow passage of the instrument,
wherein the pellets are configured to be ejected from the hollow passage in multiple directions and to be introduced into the cavity of the vertebral body as a bone replacement material, and
wherein each of the plurality of bone-replacement pellets are formed free of a through hole being provided therethrough, and wherein each of the plurality of bone-replacement pellets are configured to be pushed into a vertebral body using an ejector bar of the instrument after being placed into the hollow passage of the instrument.

2. The bone replacement as claimed in claim 1, wherein the predetermined angle is in the range of 10 to 60°.

3. The bone replacement as claimed in claim 1, wherein each pellet is defined by a plurality of edges having different lengths, the length of the longest of the different edges being in the range of 5 to 10 mm.

4. The bone replacement as claimed in claim 1, wherein each pellet is defined by a plurality of edges having different lengths, the length of the shortest of the different edges being in the range of 2 to 5 mm.

5. The bone replacement as claimed in claim 1, wherein the volume of each pellet of the bone replacement material is in the range of 13 to 239 mm$^3$.

6. The bone replacement as claimed in claim 1, wherein each pellet of the bone replacement has been subjected to chamfering.

7. The bone replacement as claimed in claim 1, wherein the bone replacement is configured to be packed into a cavity of the vertebral body using the hollow passage of the instrument.

8. The bone replacement as claimed in claim 1, wherein the bone replacement is mainly ceramic.

9. The bone replacement as claimed in claim 8, wherein the ceramic is mainly a calcium phosphate based compound.

10. The bone replacement as claimed in claim 9, wherein the Ca/P ratio of the calcium phosphate based compound is in the range of 1.0 to 2.0.

11. The bone replacement as claimed in claim 1, wherein a first pellet is configured to be placed in the hollow passage so that an inclined surface of the first pellet faces an inclined surface of the adjacent pellet.

12. The bone replacement as claimed in claim 11, wherein, when the pellets placed in the hollow passage are pushed with a push rod, the inclined surface of the first pellet pushes the inclined surface of the adjacent pellet.

13. A bone replacement, comprising:
a plurality of roughly-polyhedral pellets configured to be introduced into a hollow passage of an instrument that introduces the pellets into a cavity of a vertebral body, each pellet being defined by a plurality of surfaces including a pair of opposite surfaces that are inclined with respect to each other at a predetermined angle, and an inclined surface of a first pellet facing a correspondingly inclined surface of an adjacent second pellet when the pellets are introduced into the hollow passage of the instrument,
wherein the pellets are configured to be ejected from the hollow passage in multiple directions and to be introduced into the cavity of the vertebral body as a bone replacement material, and
wherein each of the plurality of roughly-polyhedral pellets are formed free of a through hole being provided therethrough, and wherein each of the plurality of roughly-polyhedral pellets are configured to be pushed into a vertebral body using an ejector bar of the instrument after being placed into the hollow passage of the instrument.

14. The bone replacement as claimed in claim 13, wherein the predetermined angle is in the range of 10 to 60°.

15. The bone replacement as claimed in claim 13, wherein the bone replacement is mainly ceramic.

* * * * *